United States Patent [19]

Schulz et al.

[11] Patent Number: 5,792,843
[45] Date of Patent: Aug. 11, 1998

[54] PROCESS FOR THE PRODUCTION OF ALKYL AND/OR ALKENYL OLIGOGLUCOSIDES

[75] Inventors: Paul Schulz, Wuppertal; Rainer Eskuchen, Langenfeld, both of Germany

[73] Assignee: Henkel Kommanditgesellschaft auf Aktien, Duesseldorf, Germany

[21] Appl. No.: 569,148

[22] PCT Filed: Jun. 22, 1994

[86] PCT No.: PCT/EP94/02036

§ 371 Date: Jan. 22, 1996

§ 102(e) Date: Jan. 22, 1996

[87] PCT Pub. No.: WO95/01360

PCT Pub. Date: Jan. 12, 1995

[30] Foreign Application Priority Data

Jul. 1, 1993 [DE] Germany .......................... 43 21 840.7

[51] Int. Cl.⁶ .............................. C07H 1/00; C07H 15/04; C11D 3/22

[52] U.S. Cl. ................. 536/18.6; 536/18.5; 536/120; 536/124; 510/108; 510/470

[58] Field of Search .................. 536/18.5, 18.6, 536/124, 120; 510/470, 108

[56] References Cited

U.S. PATENT DOCUMENTS 5,536,431  7/1996  Carduck et al. ................. 510/444

*Primary Examiner*—John Kight
*Assistant Examiner*—Howard C. Lee
*Attorney, Agent, or Firm*—Ernest G. Szoke; Wayne C. Jaeschke; Henry E. Millson, Jr.

[57] ABSTRACT

Alkyl and/or alkenyl oligoglucosides can be produced at high reaction rates by a process in which glucose having a particle size distribution of at least 80% in the 20 to 300 μm range is subjected to acidic acetalization with fatty alcohols. Products having a high percentage content of monoglucosides are obtained.

8 Claims, No Drawings

PROCESS FOR THE PRODUCTION OF ALKYL AND/OR ALKENYL OLIGOGLUCOSIDES

BACKGROUND OF THE INVENTION

1. Field of the Invention

This invention relates to a process for the production of alkyl and/or alkenyl oligoglucosides, in which glucose of a selected particle size is subjected to acidic acetalization with fatty alcohols in known manner, and to the use of this glucose for the production of alkyl and/or alkenyl oligoglucosides.

2. Statement of Related Art

Alkyl oligoglycosides, more particularly alkyl oligoglucosides, are nonionic surfactants which are acquiring increasing significance by virtue of their excellent detergent properties and their high ecotoxico-logical compatibility. The production and use of these substances have been described just recently in a number of synoptic articles, of which the articles by H. Hensen in Skin Care Forum, 1, (October 1992), D. Balzer and N. Ripke in Seifen-Öle-Fette-Wachse 118, 894 (1992) and B. Brancq in Seifen-Öle-Fette-Wachse 118, 905 (1992) are cited as examples.

They are normally produced from glucose which is acetalized with fatty alcohols in the presence of acidic catalysts. The catalyst is then neutralized, excess fatty alcohol is removed and the product is bleached.

Basically, acids are used as catalysts for the acetalization. Sulfuric acid, for example, is extremely effective in the condensation, but always leads to very dark-colored products which are difficult or impossible to lighten. In addition, a high content of unwanted secondary products, particularly polyglucose, is observed.

In the past, there has been no shortage of proposals for suitable acidic catalysts which it was hoped would control product distribution and, in particular, the reaction rate. For example, it is known from EP-B1 0 132 043 and EP-B1 0 132 046 (Procter & Gamble) that p-toluene sulfonic acid and, in particular, anionic surfactants in acidic form, such as for example long-chain alkylbenzene sulfonic acids, alkyl sulfonic acids and sulfuric acid semiesters of fatty alcohols and polyglycol ethers thereof, are suitable for this purpose. Similarly, U.S. Pat. No. 5,003,057 (Henkel Corp.) describes the use of naphthalene sulfonic acid. Finally, the acetalization of sugars in the presence of sulfosuccinic acid is known from EP-A 0 415 192.

However, all these known processes have the disadvantage that the reaction rate is still unsatisfactory compared with other industrial processes and results in long reactor possession times which adversely affect the economy of the process. In addition, experience has shown that the length of the reaction time gives rise to a deterioration in color quality, so that a reduction in the reaction time is desirable for this reason, too. So far as product distribution is concerned, the choice of the catalyst acid has proved to be of little relevance.

Accordingly, the problem addressed by the present invention was to provide an improved process for the production of alkyl and/or alkenyl oligoglucosides which would be free from the disadvantages mentioned above.

DESCRIPTION OF THE INVENTION

The present invention relates to a process for the production of alkyl and/or alkenyl oligoglucosides, in which glucose having a particle size distribution of at least 70% in the 20 to 300 μm range and preferably 90% in the 20 to 200 μm range is subjected to acidic acetalization with fatty alcohols in known manner.

It has surprisingly been found that the particle size of the glucose has a considerable bearing on the rate of the acetalization reaction and hence on color quality. At the same time, the process according to the invention significantly improves the selectivity of acetalization by increasing the percentage content of monoglucosides and reducing the percentage content of higher oligomers.

The invention includes the observation that glucose having a broad particle size distribution in the 20 to 200 μm range shows an optimal reaction rate so far as typical evaporation capacities are concerned.

In addition, it has proved to be of advantage in the process according to the invention to use glucose of a quality which comprises both an ultrafine particle component (<20 μm) and also a coarse particle component (>500 μm) of less than 10% by weight and preferably less than 5% by weight in either case. This measure is of particular advantage where relatively long-chain fatty alcohols are used.

Production Of The Alkyl And/Or Alkenyl Oligoglucosides

The production of alkyl and/or alkenyl oligoglucosides by acid-catalyzed acetalization of glucose with fatty alcohols—optionally via the intermediate stage of butyl glucosides—is known from a number of publications, cf. EP-A1-0 301 298 and WO 90/3977.

The glucose to be used in accordance with the invention is a commercially obtainable product, although it cannot be obtained by simple sieve analysis, even from conventional types.

Suitable fatty alcohols are $C_{6-22}$ and preferably $C_{8-16}$ fatty alcohols. Technical $C_{12-16}$ or $C_{8-10}$ fatty alcohols based on coconut oil or palm kernel oil are preferably used.

Suitable acidic catalysts are surface-active and non-surface-active systems, for example dodecanebenzene sulfonic acid, naphthalene sulfonic acid, sulfosuccinic acid, sulfoacetic acid, p-toluene sulfonic acid, methane sulfonic acid and sulfotriacetin. The catalysts may be used in quantities of 1 to 10 mEq, based on glucose.

After the acetalization, the acidic catalysts may be neutralized in known manner, more particularly by the addition of magnesium oxide and/or sodium hydroxide solution. The excess fatty alcohol is best removed in two stages by rough depletion in a falling-film evaporator and fine depletion in a thin-layer evaporator. The resulting alkyl and/or alkenyl oligoglycosides may then be made into a paste with water and/or bleached with hydrogen peroxide.

Industrial Applications

The glucose to be used in accordance with the invention, which has a particle size distribution of at least 70% in the 20 to 300 μm range, is distinguished by a particularly high reaction rate in the acetalization reaction and leads to comparatively light-colored products having a high content of monoglucosides. Accordingly, the present invention also relates to their use for the production of alkyl and/or alkenyl oligoglucosides.

The following Examples are intended to illustrate the invention without limiting it in any way.

EXAMPLES a) Reaction Rate 234 g (1.3 moles) of anhydrous glucose with a particle size distribution of 90% in the 20 to 200 or 200 to 800 μm range were introduced into a 1 liter three-necked flask equipped with a stirrer, dropping funnel and distillation column, followed by addition of 1400 g (6.5 moles) of $C_{12/14}$ coconut oil fatty alcohol (Lorol® Spezial, hydroxyl value 290; a product of Henkel KGaA, Düsseldorf, FRG). The reaction mixture was preheated to 90° C., a vacuum of 20 mbar was applied and 4 mEq—based on glucose—methane sulfonic acid were then introduced over a period of 5 minutes through the dropping funnel. After the addition (t=0), the reaction mixture was heated to 110° C. and the separation of water—as a measure of the reaction rate—was followed as a function of the reaction time. The results are set out in Table 1.

b) Product Composition

The crude reaction product was neutralized, transferred to a vacuum distillation apparatus and the excess fatty alcohol was distilled off at a temperature of 180° C under a reduced pressure of 5 mbar. The products were then bleached with 1% by weight hydrogen peroxide, based on the products, at pH 9. The composition of the products is shown in Table 2.

TABLE 1

| | | Reaction rate | | |
|---|---|---|---|---|
| Ex. | Particle size μm | t (30) mins. | t (50) mins. | t (70) mins. |
| 1 | 20–200 | 42 | 63 | 100 |
| C1 | 200–800 | 80 | 125 | 160 |

Legend:
t (x) = Time required for removal of x% of the theoretical quantity of water of reaction

TABLE 2

| | | Product composition Percentages as % by weight | | | | | |
|---|---|---|---|---|---|---|---|
| | | | Monoglucoside (%) | | | | |
| EX. | Particle size μm | MG | C12-α-GP | C12-β-GP | C12-GF | DG % | Rest % |
| 2 | 20–200 | 59 | 33 | 11 | 2 | 14 | 40 |
| C4 | 200–800 | 51 | 30 | 10 | 1 | 15 | 44 |

Legend:
MG = Monoglucoside
DG = Diglucoside
C12-α-GP = C12 α-Glucopyranoside
C12-β-GP = C12 β-Glucopyranoside
C12-GF = C12 Glucofuranoside

We claim:

1. In the production of alkyl and/or alkenyl oligoglucosides in which glucose is subjected to acidic acetalization with a fatty alcohol, the improvement wherein the glucose has a) a particle size distribution of at least 90% in the 20 to 200 μm range, and b) an ultrafine component (<20 μm) of less than 10% by weight, and a coarse component (>500 μm) of less than 10% by weight.

2. The process of claim 1 wherein the ultrafine component and the coarse component are both present in less than 5% by weight.

3. The product of the process of claim 1 wherein the percentage by weight of alkyl and/or alkenyl monoglucoside therein is at least about 59% and the percentage of alkyl and/or alkenyl diglucoside therein is not greater than about 14%.

4. A process for the production of alkyl and/or alkenyl oligoglucosides comprising the steps of A) acetalizing glucose with at least one fatty alcohol in the presence of an acidic catalyst, wherein the glucose has
      a) a particle size distribution of at least 90% in the 20 to 200 μm range, and
      b) an ultrafine component (<20 μm) of less than 10% by weight, and a coarse component (>500 μm) of less than 10% by weight; and B) isolating an alkyl and/or alkenyl ologoglucoside from the resulting reaction mixture wherein the percentage by weight of alkyl and/or alkenyl monoglucoside therein is at least about 59% and the percentage of alkyl and/or alkenyl diglucoside therein is not greater than about 14%.

5. The process of claim 4 wherein in step A) the at least one fatty alcohol contains from 6 to 22 carbon atoms.

6. The process of claim 5 wherein the at least one fatty alcohol contains from 8 to 16 carbon atoms.

7. The process of claim 5 wherein technical $C_{12-16}$ fatty alcohols are used in step A).

8. The process of claim 5 wherein technical $C_{8-10}$ fatty alcohols are used in step A).

* * * * *